United States Patent
Luecke et al.

(10) Patent No.: US 8,246,247 B2
(45) Date of Patent: *Aug. 21, 2012

(54) COMPUTED TOMOGRAPHY ROTOR RIGIDIFIED BY A COMPOSITE MATERIAL WITH SHAPED BODIES THEREIN

(75) Inventors: Daniela Luecke, Germering (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 203 days.

This patent is subject to a terminal disclaimer.

(21) Appl. No.: 12/533,228

(22) Filed: Jul. 31, 2009

(65) Prior Publication Data

US 2010/0027759 A1 Feb. 4, 2010

(30) Foreign Application Priority Data

Aug. 1, 2008 (DE) .................. 10 2008 036 017

(51) Int. Cl.
*H05G 1/02* (2006.01)

(52) U.S. Cl. .................. 378/197; 378/4; 250/363.02

(58) Field of Classification Search ............. 378/4, 197; 250/363.02
See application file for complete search history.

(56) References Cited

U.S. PATENT DOCUMENTS

| | | | | |
|---|---|---|---|---|
| 5,031,198 A * | 7/1991 | Deucher et al. ............ 378/4 |
| 5,039,057 A * | 8/1991 | Prechter et al. ............ 248/664 |
| 5,176,868 A | 1/1993 | Davis |
| 5,620,791 A * | 4/1997 | Dwivedi et al. ............ 428/323 |
| 5,703,921 A * | 12/1997 | Fujita et al. ............ 378/4 |
| 5,866,648 A | 2/1999 | Saito et al. |
| 5,972,264 A * | 10/1999 | Malekmadani et al. ...... 264/102 |
| 6,337,894 B1 * | 1/2002 | Tybinkowski et al. ......... 378/4 |
| 6,590,953 B2 * | 7/2003 | Suzuki et al. ............ 378/15 |
| 6,607,358 B2 * | 8/2003 | Finn et al. ............ 416/224 |
| 6,940,941 B2 * | 9/2005 | Gregerson et al. ............ 378/4 |
| 7,406,149 B2 * | 7/2008 | Yokoyama et al. ............ 378/15 |
| 7,438,471 B2 * | 10/2008 | Tybinkowski et al. ......... 378/198 |
| 7,494,275 B2 * | 2/2009 | Buttner et al. ............ 378/193 |
| 7,661,881 B2 * | 2/2010 | Gregerson et al. ............ 378/197 |
| 7,927,013 B2 * | 4/2011 | Luecke et al. ............ 378/189 |
| 7,997,797 B2 * | 8/2011 | Luecke et al. ............ 378/197 |
| 8,085,896 B2 * | 12/2011 | Luecke et al. ............ 378/4 |
| 2006/0018437 A1 * | 1/2006 | Russinger ............ 378/197 |
| 2007/0064863 A1 * | 3/2007 | Buttner et al. ............ 378/4 |

(Continued)

FOREIGN PATENT DOCUMENTS

DE 42 14 858 C1 2/1994
DE 20 2006 004 118 U1 8/2007

OTHER PUBLICATIONS

U.S. Appl. No. 12/533,213, filed Jul. 31, 2009.

(Continued)

*Primary Examiner* — Thomas R Artman
(74) *Attorney, Agent, or Firm* — Schiff Hardin LLP

(57) ABSTRACT

In a rotor for a gantry of a computed tomography apparatus, as well as a manufacturing method for such a rotor, the rotor is manufactured as to contain shaped bodies (at least in segments of the rotor) produced from a composite material. By the integration of such shaped bodies with high strength and rigidity, the rotor can be stabilized in a targeted manner in the regions in which high stress values that arise upon rotation of the rotor.

15 Claims, 3 Drawing Sheets

U.S. PATENT DOCUMENTS

| | | | |
|---|---|---|---|
| 2008/0274366 A1* | 11/2008 | Noguchi et al. | 428/545 |
| 2009/0067571 A1* | 3/2009 | Lacey | 378/19 |
| 2010/0025590 A1* | 2/2010 | Luecke et al. | 250/363.05 |
| 2010/0027757 A1* | 2/2010 | Luecke et al. | 378/197 |
| 2010/0027758 A1* | 2/2010 | Luecke et al. | 378/197 |
| 2010/0239428 A1* | 9/2010 | Carrier et al. | 416/230 |

OTHER PUBLICATIONS

U.S. Appl. No. 12/533,198, filed Jul. 31, 2009.

U.S. Appl. No. 12/533,184, filed Jul. 31, 2009.

U.S. Appl. No. 12/533,148, filed Jul. 31, 2009.

* cited by examiner

COMPUTED TOMOGRAPHY ROTOR RIGIDIFIED BY A COMPOSITE MATERIAL WITH SHAPED BODIES THEREIN

RELATED APPLICATIONS

The subject matter of the present application is related to the subject matter of an application designated with Ser. No. 12/533,198 entitled Rigid Computed Tomography Rotor and Method for the Manufacture Thereof, and an application designated with Ser. No. 12/533,198 entitled Computed Tomography Rotor Rigidified by a Metal Matrix Material, both filed simultaneously herewith.

BACKGROUND OF THE INVENTION

1. Field of the Invention

The present invention concerns a rotor for a gantry of a computed tomography apparatus, as well as a manufacturing method for such a rotor.

2. Description of the Prior Art

Computed tomography apparatuses enable the reconstruction of three-dimensional slice or volume images of an examination region for diagnostic purposes. The reconstruction of an image ensues on the basis of projections of an examination region that are acquired by irradiating a subject with an x-ray fan beam from different projection directions by rotation of an acquisition device so that measurement data are acquired for parallel projections in an angle range of at least 180 degrees plus the fan angle for reconstruction of an image. To achieve the rotation of the data acquisition device, the computed tomography apparatus has a gantry that has a stationary frame and a rotor arranged such that it can rotate by means of a rotating bearing device. The image data acquisition device is mounted on the rotor. The rotor has been produced conventionally as a cast part made of an aluminum alloy AlZn10SiMg and has a rotor wall in the form of an annular disc and a retention ring running along its outer periphery for mounting the components of the acquisition device. The wall thicknesses of such rotors vary between 15 and 20 mm.

To avoid movement artifacts in the reconstructed image that can arise due to patient or organ movements, it is sought to select the time window for acquisition of the projections required for reconstruction to be as small as possible by the use of high rotation speeds. Rotation speeds of 210 R/min are achieved in current computed tomography apparatuses. In the future the rotation speeds are expected to be increased to at least 300 R/min.

Due to a combination of high rotation speed, large rotation radius and high rotation mass, the rotor represents a highly mechanically stressed component that, in addition to accommodating the stresses that are incurred, must also reliably maintain the positions of x-ray tubes and detectors, since position shifts of the components of more than 0.15 mm can lead to a significant degradation of the image quality.

Significant primary requirements for the rotor of a gantry are accordingly not only a high strength to transfer the forces, but also a high rigidity in order to keep deformations of the rotor (and thus the position shifts of the components of the acquisition device) below the allowable limits, given a simultaneously low weight.

An additional thickening of the existing design would be necessary in order to achieve rotation speeds of 300 R/min and more while keeping the same material. The consequence would be a weight increase of the rotor. Components to drive the rotor and the stationary part of the gantry would thereby also have to be adapted to the greater weight. This approach also has the disadvantage of causing a weight and volume increase of the entire gantry.

SUMMARY OF THE INVENTION

An object of the present invention is to provide a rotor of a gantry of a computed tomography apparatus such that the rotor can be operated without loss of quality in the generation of slice or volume images even at high rotor rotation speeds, in particular at rotor rotation speeds of 300 R/min or more. It is also an object of the invention to provide a method for manufacturing such a rotor.

The invention is based on the insight that the rotor is locally severely loaded very differently during the rotation, such that a very limited local reinforcement of the rotor already contributes to a significant increase of the rigidity and strength of the entire structure. For example, those regions of the rotor in which high stress values arise due to discontinuities of the rotor contour, or due to a mounting of components of an image data acquisition device of a computed tomography apparatus, can be partially reinforced. This reinforcement can ensue by means of a composite material in which the matrix is additionally mechanically stabilized by a reinforcement material introduced into the matrix. This is based on the additional insight that a local reinforcement of the rotor can be achieved in a particularly simple way by prefabricating the composite material as a shaped body.

The rotor according to the invention for a gantry of a computed tomography apparatus is appropriately locally reinforced at least in segments with shaped bodies produced from a composite material.

By the integration of shaped bodies, a very effective local reinforcement of the rotor is achieved since the shaped bodies can be manufactured in separate processing steps under the conditions according to which the composite material exhibits a high purity, a homogeneous distribution and alignment of the reinforcement material, a homogeneous bonding agent distribution, and a low binding agent content.

The shaped bodies are essentially hollow in design and have infiltration openings. An optimal penetration of the shaped body with the base material from which the rotor is produced is thereby ensured, and thus an optimal integration of the shaped body into the rotor.

In an embodiment of the invention, the composite material has a reinforcement material in the form of short fibers and/or long fibers. Since fibers can accommodate forces, in particular along their alignment, this reinforcement material is suitable for situations in which forces act in an essentially unidirectional manner.

The fibers are advantageously carbon fibers. Carbon fibers have a low weight, are simple to manufacture, are highly durable and can be processed further in a simple manner into two-dimensional or three-dimensional textiles. Complex fiber arrangements that accommodate the course of force paths given an anisotropic stress can also be achieved by textile techniques, for example weaving or spinning. Naturally, it is also possible to use other fibers (for example aramid fibers) instead of or in combination with carbon fibers.

In an embodiment of the invention, the composite material has a reinforcement material in the form of particles. Particles as the reinforcement material are particularly suitable when the forces arising upon rotation of the rotor have no preferential direction.

The particles are advantageously produced from silicon carbide or from a metal alloy, in particular from an aluminum alloy. An optimal reinforcement is achieved when the volume proportion of the particles is between 10% and 20% of the total rotor volume.

In another embodiment of the invention, the composite material has a metal matrix, in particular a matrix made of an aluminum alloy.

As an alternative, the composite material can have a polymer matrix, in particular an epoxy matrix. The curing of the resin ensues in a few minutes or hours by the addition of an accelerator, such that the manufacturing time is also decreased to a significant degree with the use of epoxy resin.

The shaped bodies are advantageously aligned along force paths that arise upon rotation of the rotor. Regions of the rotor in which forces exist with a preferential direction can be stabilized particularly well by the introduction of the shaped bodies. Spatial force paths and the alignment of the shaped bodies associated with said paths can be determined experimentally or numerically using appropriate mathematical models in the form of a simulation.

In an embodiment of the invention, depending on their position in the rotor, the shaped bodies have recesses for the introduction of mounting bores. In this way it can be ensured that machine processing of the rotor does not lead to damage to the composite material (and thus to a destabilization of the rotor structure).

A manufacturing method to manufacture a rotor according to the invention includes the following method steps:

a) the shaped bodies are inserted into a work piece, b) the matrix of the composite material is subsequently injected into the work piece by at least one opening, wherein venting takes place via at least one additional opening in the work piece, and the injection pressure is selected so that the matrix flows through the shaped bodies via the infiltration openings.

c) A curing ensues by heating the composite material.

The heating is advantageously implemented by means of a heating element integrated into the work piece. It is also possible to use a microwave technology with which the matrix is directly heated by electromagnetic radiation.

DESCRIPTION OF THE PREFERRED EMBODIMENTS

Figure 1:
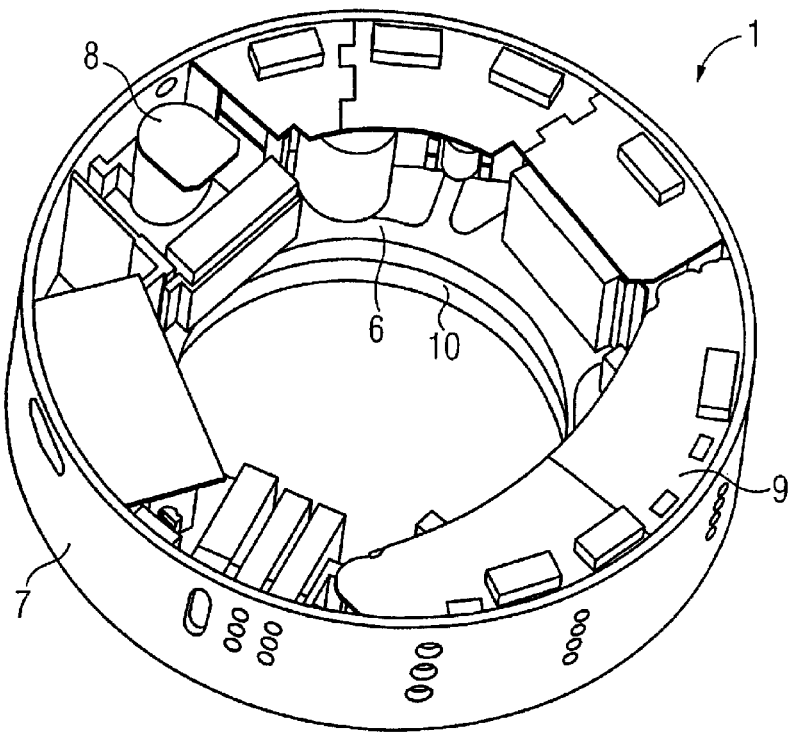
FIG. 1 is a first perspective view of a rotor for a gantry of a computed tomography apparatus with components of an acquisition device.
Figure 2:
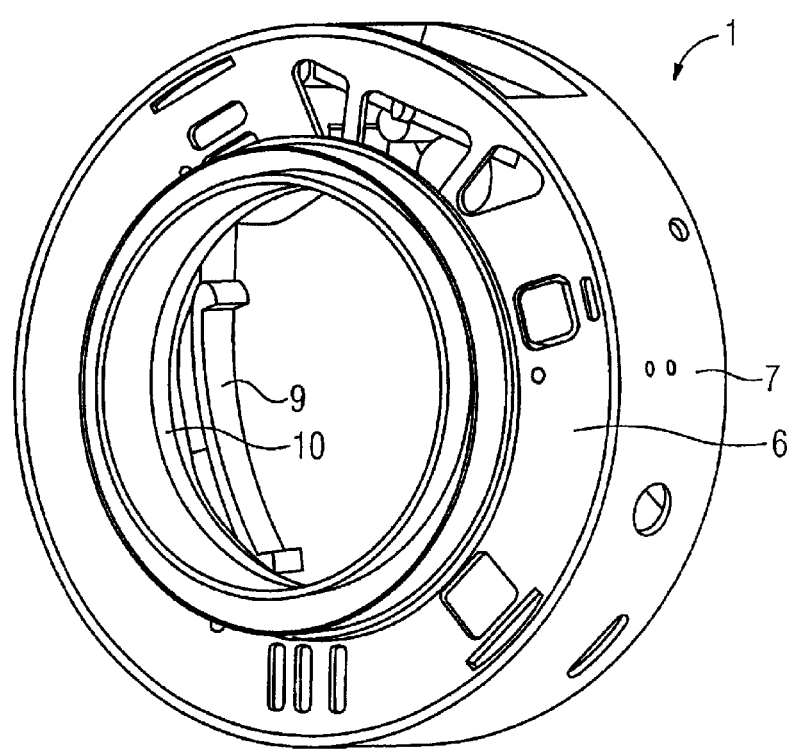
FIG. 2 is a second perspective view of the rotor for a gantry of a computed tomography apparatus with components of an acquisition device.

Two different perspective views of a rotor 1 for a gantry of a computed tomography apparatus shown are shown in FIG. 1 and FIG. 2. The rotor 1 has a rotor wall 3 in the form of a ring rim 6 and a retention ring 7 running on the outer circumference of the rotor wall 3 for mounting components of a computed tomography image data acquisition device. The acquisition device essentially has an x-ray radiator in the form of an x-ray tube 8 and a detector 9 arranged opposite the radiator. Moreover, the ring rim 6 has on its inner circumference components of a rotation bearing device 10 that interact with correspondingly arranged components of a rotation bearing device 10 on a stationary part of the gantry so that the rotor 1 is arranged such that it can rotate. The rotation speeds of the rotor 1 are presently approximately 210 R/min and will in the future increase to at least 300 R/min. The rotor 1 represents a highly stressed structural part due to the combination of high rotation speed, large rotation radius and high rotation mass of the components 5, 6 of the acquisition device that are arranged on the retention ring 4. The rotor 1 must not only have a high strength to accommodate the stresses occurring during a rotation movement of the rotor 1, but it must also additionally be ensured that the positions of x-ray tube 8 and detector 9 do not significantly change in relation to the scan plane. A position shift of over 0.15 mm would already lead to a degradation of the image quality since the projection conditions forming the basis of the reconstruction of an image are not maintained.

Discontinuities of the rotor contour and spot connections for mounting components of the acquisition device of the computed tomography apparatus lead to the situation that the rotor 1 is severely stressed very differently locally during the rotation.

Figure 3:
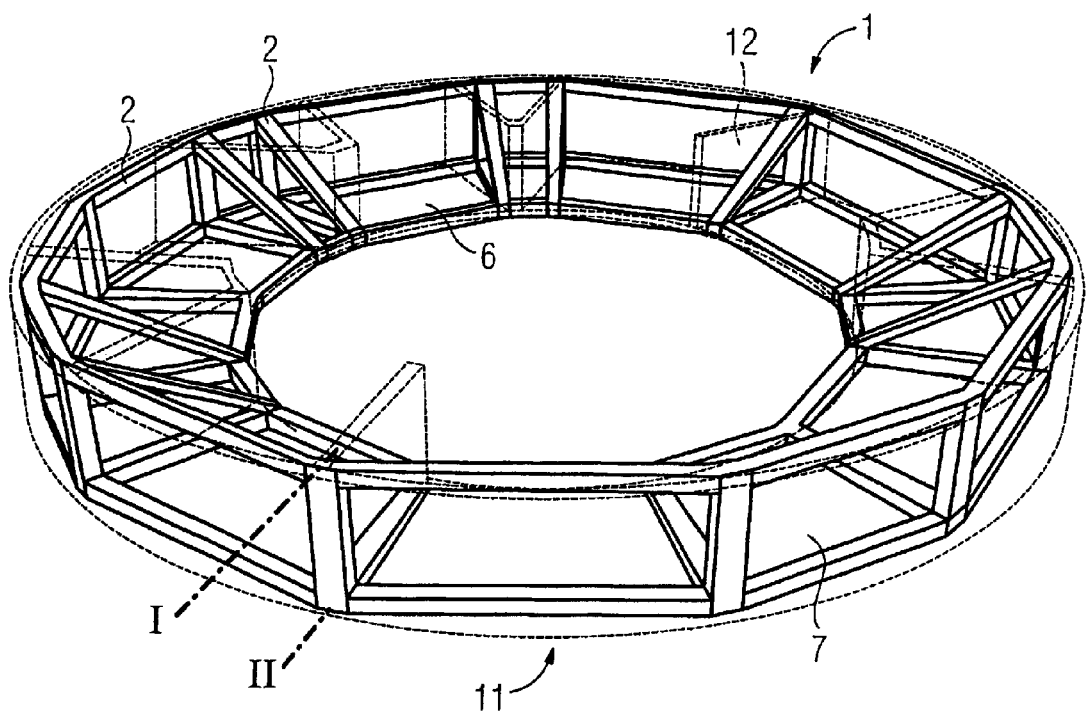
FIG. 3 is a perspective view of a rotor for a gantry that locally has shaped bodies produced from a composite material

A rotor 1 according to the invention is shown in a perspective view in FIG. 3. To accommodate the very high stress values occurring in small regions of the rotor 1, the rotor 1 is locally reinforced in a targeted manner with shaped bodies 2 produced from a composite material 3 shown in FIG. 4. For clarity, only two shaped bodies 2 are provided with a reference character in FIG. 3. The ring rim 6 fashioned as a rotor wall and the retention ring 7 running on its outer circumference for the mounting of the components of the acquisition devices are partially reinforced by shaped bodies 2. The shaped bodies 2 have a bar shape in this exemplary embodiment. A discontinuity of the rotor contour exists in the transition region between the retention ring 7 and the ring rim 6. For example, the rotor structure is locally reinforced by means of shaped bodies 2 at precisely this region 11, as shown in FIG. 3. The ribs 12 arranged between the ring rim 6 and the retention ring 7 and that brace the rotor 1 during rotation are also provided with such shaped bodies 2 for targeted accommodation of tensile stresses arising upon rotation.

Figure 4:
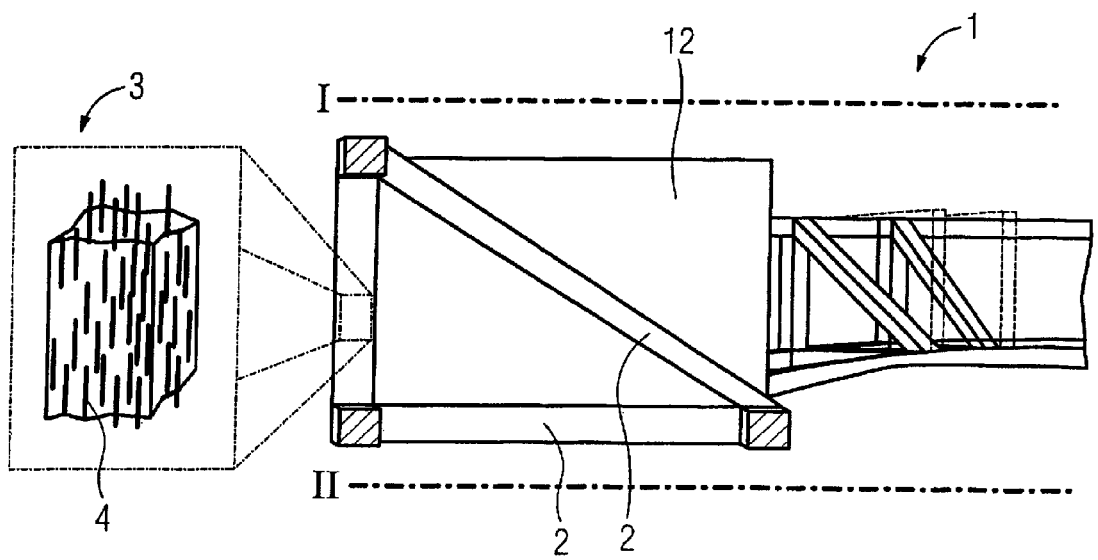
FIG. 4 is a perspective partial view of a portion of the rotor from FIG. 2 with a section through a plane spanned by a rib.

FIG. 4 shows a partial view of the rotor 1 shown in FIG. 3 with a section through the plane spanned by the straight lines I and II. A part of a shaped body 2 is schematically depicted in enlarged form. The composite material 3 used to produce the shaped body 2 has fibers 4 (in this exemplary embodiment, short fibers) that are produced from silicon carbide (SiC) or aluminum oxide (Al2O3), for example. These fibers are ceramic fibers that possess a very good oxidation resistance and a low reactivity with metals. For this reason, these fibers 4 are particularly suitable for the production of a composite material which possesses a metal matrix. Moreover, these fibers 4 are characterized by allowing cost-effective manufacture and a good additional processing. They also have a low thermal expansion and a low thermal and electrical conductivity. Due to these advantageous material properties, these fibers are particularly suitable for reinforcement of a rotor 1. A metal alloy (in particular an aluminum alloy) can advantageously be used as a metal matrix.

One possible production of the shaped bodies essentially includes the following method steps: the fibers 4 are initially dispersed in water, 10 g to 40 g are typically added to one liter. The fibers 4 are stabilized via addition of silica sol (SiO2) in that they form a thin hydrate envelope. An accumulation of silica sol is thereby prevented. A second binding agent component is subsequently added to the suspension. The second binding agent component thereby represents a cationic starch solution which, among other things, leads to the solids breaking up. The shaping of the shaped bodies 2 subsequently ensues by means of a vacuum press method. The suspension is hereby filled into a mold with porous floor. The fibers align between ram and mold floor due to the pressing. The shaped body is subsequently heated for curing.

In addition to fibers, particles can also be used as a reinforcement material. The particles are advantageously produced from silicon carbide or a metal alloy, in particular an aluminum alloy. Particles as a reinforcement material are in particular suitable when no preferential direction of the forces arising upon rotation of the rotor 1 predominates. Shaped bodies 2 with a composite material 3 that is reinforced with particles are produced according to the previously described method. While a particle content of 20% should not be exceeded in large-area casting of molten masses with added particles, this can be 50% or more in a shaped body 2. A particularly high stability of the composite material 3 (and thus of the locally reinforced region of the rotor 1) is thereby achieved.

It would likewise be conceivable to use a mixture of particles and fibers 4 as a reinforcement material for a composite material 3. This case called a hybrid shaped body. Reinforcement properties that lie between those of pure fiber reinforcement and those of pure particle reinforcement can be achieved with such a hybrid shaped body.

A composite material 3 with a polymer matrix (for example with an epoxy matrix) can naturally also be used instead of a composite material 3 with a metal matrix. In this case fibers 4 made of carbon would be suitable as a reinforcement material.

Figure 5:
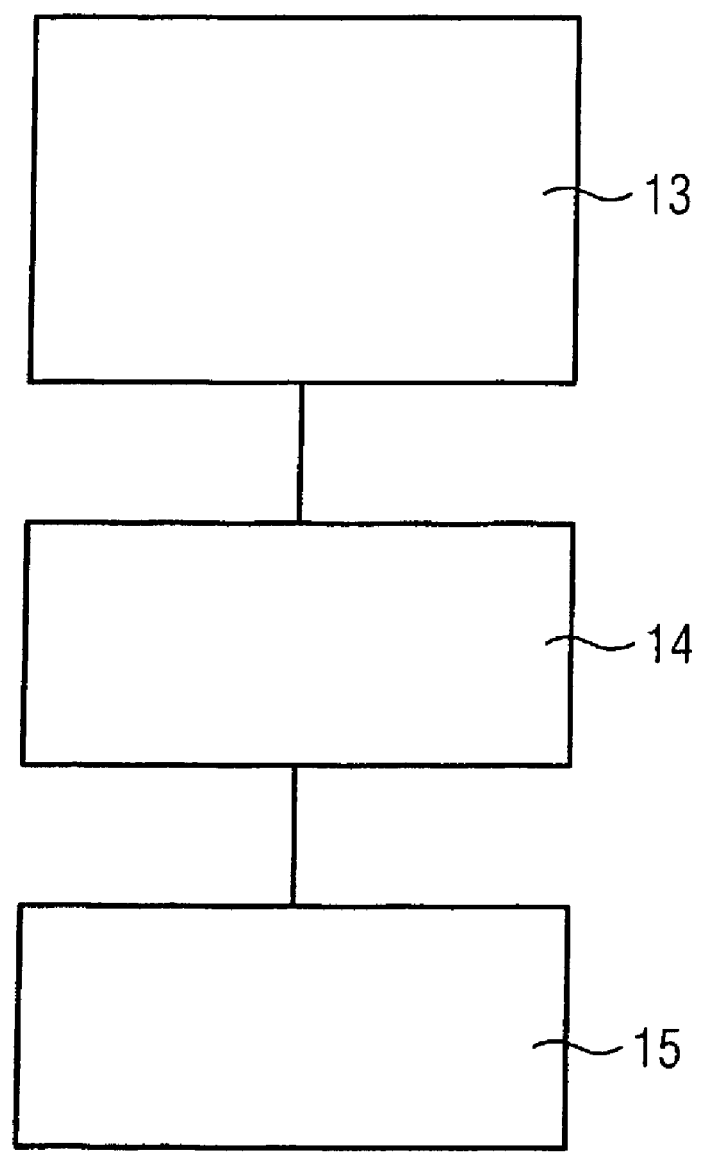
FIG. 5 is a block diagram of an embodiment of a method step for the production of the rotor shown in FIG. 3.

An additional, advantageous manufacturing of the rotor 1 with the previously described shaped bodies 2 essentially includes the following method steps, shown in FIG. 5. In a first method step 13, the shaped bodies 2 are initially placed in a work piece for the pouring of the rotor 1. The shaped bodies 2 are arranged in the work piece so that they are essentially aligned along force paths arising upon rotation of the rotor 1. In a second method step 14, the matrix of the composite material 3 is subsequently injected into the work piece via at least one opening. The venting occurs via at least one additional opening in the work piece. The injection pressure is selected so that the matrix flows through the shaped bodies 2 via the provided infiltration openings. In a third method step 15, the curing subsequently ensues by heating the composite material 3. The heating is alternately implemented either by a heating element integrated into the work piece or by the use of microwave technology.

In summary, the invention concerns a rotor 1 for a gantry of a computed tomography apparatus, as well as a manufacturing method for such a rotor 1. The rotor 1 according to the invention is produced at least in segments with shaped bodies 2 produced from a composite material. By integration of shaped bodies 2 with high strength and rigidity, the rotor 1 can be stabilized in a targeted manner in the regions in which high stress values exist upon rotation of the rotor 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rotor for a gantry of a computed tomography apparatus, comprising:
   a rotor structure configured to mount computed tomography image data acquisition components thereon, said rotor structure being configured to rotate around a rotation center, with rotation of said rotor structure around said rotation center with said components mounted thereon producing localized force stresses in said rotor structure; and
   said rotor structure comprising a plurality of structural bars joined together in a structural configuration, at least some of said structural bars comprising a composite, reinforcement material formed by carbon fibers selected from the group consisting of short fibers and long fibers, each of said shaped-bodies structural bars forming a structural element of said rotor structure and having a shape, orientation and location in said rotor structure that reinforces said rotor structure against said localized force stresses; and
   said structural configuration comprising a plurality of right triangles and trapezoids formed by said structural bars, each of said right triangles comprising a base and a hypotenuse and the respective bases of said right triangles defining a base plane and each of said triangles being oriented at 90° relative to said base plane, and the respective hypotenuses of said right triangles defining a hypotenuse plane, and said trapezoids being located in said hypotenuse plane.

2. A rotor as claimed in claim 1 wherein said structural bars are hollow and comprise infiltration openings for said composite material.

3. A rotor as claimed in claim 1 wherein said composite, reinforcement material, in addition to said carbon fibers, also comprises a particles.

4. A rotor as claimed in claim 3 wherein said particles are comprised of a material selected from the group consisting of silicon carbide and metal alloys.

5. A rotor as claimed in claim 3 wherein said particles are comprised of an aluminum alloy.

6. A rotor as claimed in claim 3 wherein said composite material comprises a metal matrix.

7. A rotor as claimed in claim 6 wherein said metal matrix is comprised of an aluminum alloy.

8. A rotor as claimed in claim 1 wherein said composite material comprises a polymer matrix.

9. A rotor as claimed in claim 8 wherein said polymer matrix is an epoxy matrix.

10. A rotor as claimed in claim 1 wherein said structural bars are aligned in said rotor structure along force paths that arise during rotation of said rotor structure around said rotation center.

11. A rotor as claimed in claim 1 wherein at least some of said structural bars comprise recesses therein allowing introduction of mounting bores therein for mounting said components to said rotor structure.

12. A computed tomography gantry comprising:
    a stationary frame;
    a rotor mounted to rotate in said stationary frame around a rotation center;
    a plurality of computed tomography image acquisition components mounted on said rotor for co-rotation therewith around said rotation center, thereby causing localized force stressed to arise in said rotor;
    said rotor comprising a rotor structure comprising a plurality of structural bars joined together in a structural configuration, at least in each of segments of said rotor structure, a composite, reinforcement material formed by carbon fibers selected from the group consisting of short fibers and long fibers, each of said structural bars forming a structural element of said rotor structure and having a shape, orientation and location in said rotor structure that reinforces said rotor structure against said localized force stresses; and said structural configuration comprising a plurality of right triangles and trapezoids formed by said structural bars, each of said right triangles comprising a base and a hypotenuse and the respective bases of said right triangles defining a base plane and each of said triangles being oriented at 90° relative to said base plane, and the respective hypotenuses of said right triangles defining a hypotenuse plane, and said trapezoids being located in said hypotenuse plane.

13. A method for manufacturing a rotor of a computed tomography apparatus, comprising the steps of:

forming a rotor structure of a plurality of structural bars in a workpiece to produce configured to a give said rotor structure a structural configuration allowing mounting of a plurality of computed tomography image acquisition components on said rotor structure for rotation around a rotation center, thereby producing localized force stresses in said rotor structure;

forming said structural bars of said rotor structure, by injecting a matrix of a composite, reinforcement material, formed by carbon fibers selected from the group consisting of short fibers and long fibers, into said workpiece through at least one opening, and venting through at least one additional opening of said workpiece, at a pressure causing said matrix to flow through said structural bars via infiltration openings in said shaped bodies structural bars to cause said structural bars to be present in said rotor structure with a shape, distribution and orientation that reinforces said rotor body against said localized force stresses;

forming said structural configuration as a plurality of right triangles and trapezoids formed by said structural bars, each of said right triangles have a base and a hypotenuse, and the respective bases of said right triangles defining a base plane, and orienting said right triangles at 90° relative to said base plane, and the respective hypotenuses of said right triangles defining a hypotenuse plane, and locating said trapezoids in said hypotenuse plane; and curing said matrix of said composite material with said structural bars therein by heating said composite, reinforcement material.

14. A method as claimed in claim 13 comprising heating said composite material by a heating element integrated into said workpiece.

15. A method as claimed in claim 13 comprising heating said composite material by a microwave technology.

* * * * *